(12) United States Patent
Melkent et al.

(10) Patent No.: US 7,429,264 B2
(45) Date of Patent: Sep. 30, 2008

(54) MINIMALLY INVASIVE DEPLOYABLE CUTTING INSTRUMENT

(75) Inventors: Anthony J. Melkent, Memphis, TN (US); Roy Lim, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 526 days.

(21) Appl. No.: 10/868,153

(22) Filed: Jun. 15, 2004

(65) Prior Publication Data

US 2005/0277971 A1    Dec. 15, 2005

(51) Int. Cl.
*A61B 17/22* (2006.01)
(52) U.S. Cl. ...................... 606/159; 606/170
(58) Field of Classification Search .............. 606/167, 606/170, 80, 84, 159, 180, 185; 604/108, 604/109, 523; 30/346, 351, 152, 158, 169, 30/287, 304
See application file for complete search history.

(56) References Cited

U.S. PATENT DOCUMENTS

| | | | | |
|---|---|---|---|---|
| 837,085 | A * | 11/1906 | Loar ........................ | 604/108 |
| 2,490,397 | A | 12/1949 | Aked | |
| 2,959,109 | A | 11/1960 | Buchan | |
| 3,318,175 | A | 5/1967 | Cogsdill | |
| 3,702,611 | A * | 11/1972 | Fishbein ..................... | 606/81 |
| 4,357,846 | A | 11/1982 | Primo | |
| 5,015,255 | A | 5/1991 | Kuslich | |
| 5,062,845 | A | 11/1991 | Kuslich et al. | |
| 5,133,725 | A * | 7/1992 | Quadri ....................... | 606/159 |
| 5,398,360 | A * | 3/1995 | Alexander .................... | 7/158 |
| 5,445,639 | A | 8/1995 | Kuslich et al. | |
| 5,928,239 | A | 7/1999 | Mirza | |
| 6,190,414 | B1 | 2/2001 | Young et al. | |
| 6,224,604 | B1 | 5/2001 | Suddaby | |
| 6,383,188 | B2 * | 5/2002 | Kuslich et al. ............... | 606/80 |
| 6,402,770 | B1 * | 6/2002 | Jessen ....................... | 606/170 |
| 6,682,534 | B2 | 1/2004 | Patel et al. | |
| 6,726,690 | B2 | 4/2004 | Eckman | |
| 2001/0034526 | A1 | 10/2001 | Kuslich et al. | |
| 2002/0068974 | A1 | 6/2002 | Kuslich et al. | |
| 2002/0165550 | A1 | 11/2002 | Frey et al. | |
| 2003/0135218 | A1 * | 7/2003 | Eckman ...................... | 606/79 |
| 2003/0181915 | A1 | 9/2003 | Serhan | |
| 2003/0216716 | A1 | 11/2003 | Desarzens | |
| 2003/0220645 | A1 | 11/2003 | Suddaby | |
| 2004/0215197 | A1 | 10/2004 | Smith et al. | |

FOREIGN PATENT DOCUMENTS

| | | |
|---|---|---|
| DE | 38 40 466 A1 | 6/1990 |
| DE | 201 12 539 U1 | 10/2001 |
| EP | 1 346 694 A2 | 9/2003 |

* cited by examiner

*Primary Examiner*—Todd E Manahan
*Assistant Examiner*—Ryan Severson
(74) *Attorney, Agent, or Firm*—Krieg DeVault LLP

(57) ABSTRACT

Instruments and methods for cutting tissue are disclosed. The instruments include one or more cutting members movable from a reduced profile undeployed position for insertion to the operative site to a deployed position where the cutting members can be manipulated to cut tissue material at the operative site.

36 Claims, 7 Drawing Sheets

MINIMALLY INVASIVE DEPLOYABLE CUTTING INSTRUMENT

BACKGROUND

Surgery for a patient can be painful and traumatic, particularly in the affected area of the patient's body. To accommodate insertion of surgical instruments, sufficient dissection and/or retraction of muscle tissue, nerve tissue, vasculature tissue and other tissue must be made to allow passage of the instruments therethrough.

Surgical instruments can include sharp elements which can cut or cause trauma to tissue in the approach to and adjacent the surgical site. Tissue dissection and retraction may be increased to avoid contact between the instrument and the tissue in the approach to the surgical site. Additionally, delicate anatomical structures may be present at or near the surgical site. Additional instruments or other precautions may be required to protect such tissue, and these additional measures may limit or inhibit access to the surgical site.

For spinal surgical procedures, positioning surgical instruments in a spinal disc space can require difficult maneuvering and gesturing of surgical instruments. Sufficient time, effort and care during the surgery must be devoted to the positioning and use such instruments to obtain the desired result while minimizing the trauma and effect to tissue or other anatomical structures in the approach to and adjacent the disc space. There remains a need for instruments and methods that can be employed for preparing a surgical site that minimize tissue dissection and retraction, and also exposure of the anatomical structures at the surgical site to sharp elements of the instruments.

SUMMARY

A cutting instrument is provided that includes a cutting member movable between deployed and undeployed positions. In the undeployed position, the at least one cutting member is positionable to a surgical site without exposing the anatomical structures to sharp edges of the cutting member. In the deployed position, the cutting member includes at least one cutting blade for removal of bone and other tissue in or adjacent a spinal disc space.

DESCRIPTION OF THE ILLUSTRATED EMBODIMENTS

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated device and any such further applications of the principles of the invention as illustrated herein are contemplated as would normally occur to one skilled in the art to which the invention relates.

Figures 1, 2:
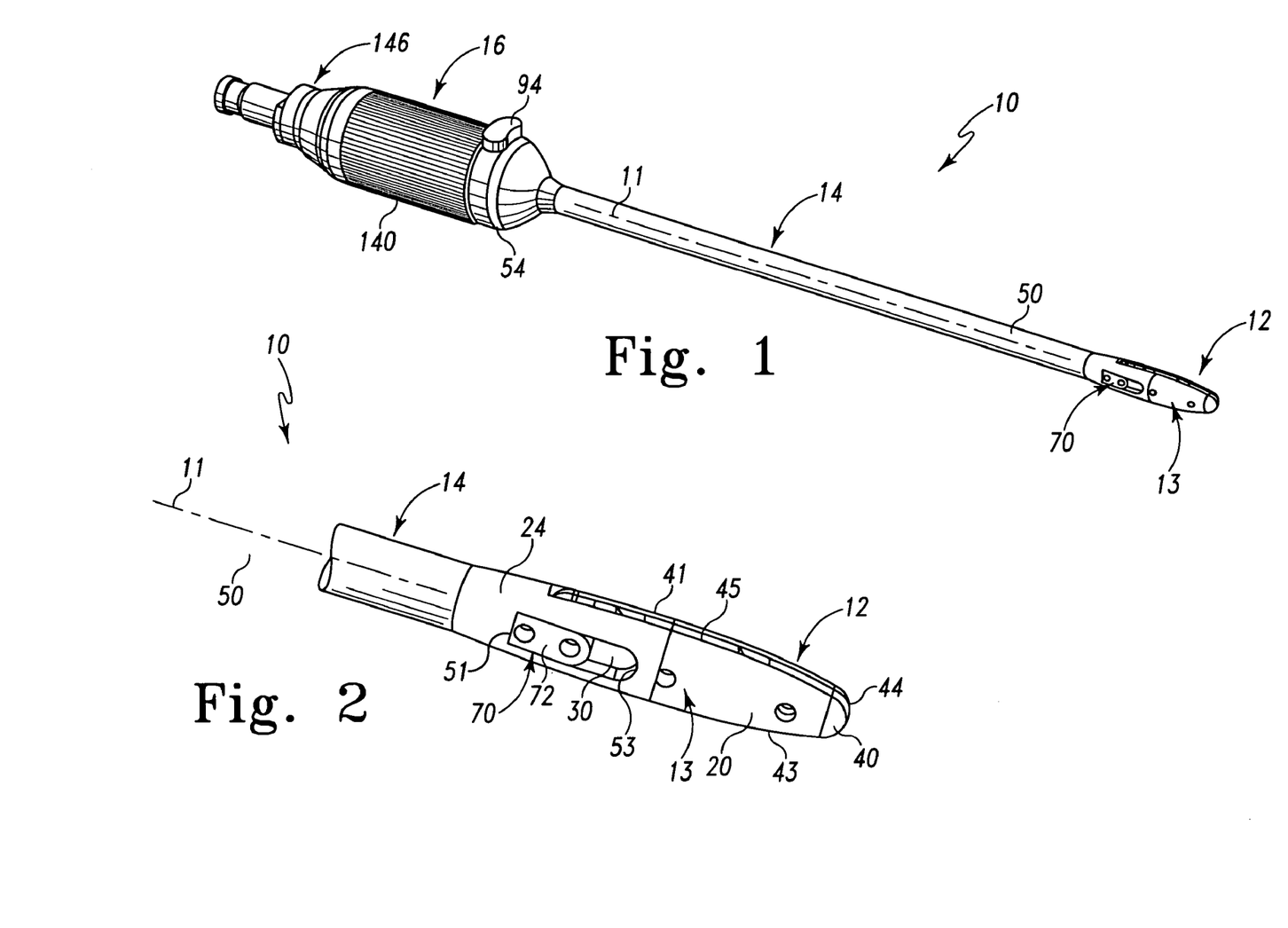
FIG. 1 is a perspective view of one embodiment of a cutting instrument in an undeployed position.
FIG. 2 is a perspective view of the distal portion of the cutting instrument of FIG. 1 in an undeployed position.
Figures 3, 4:
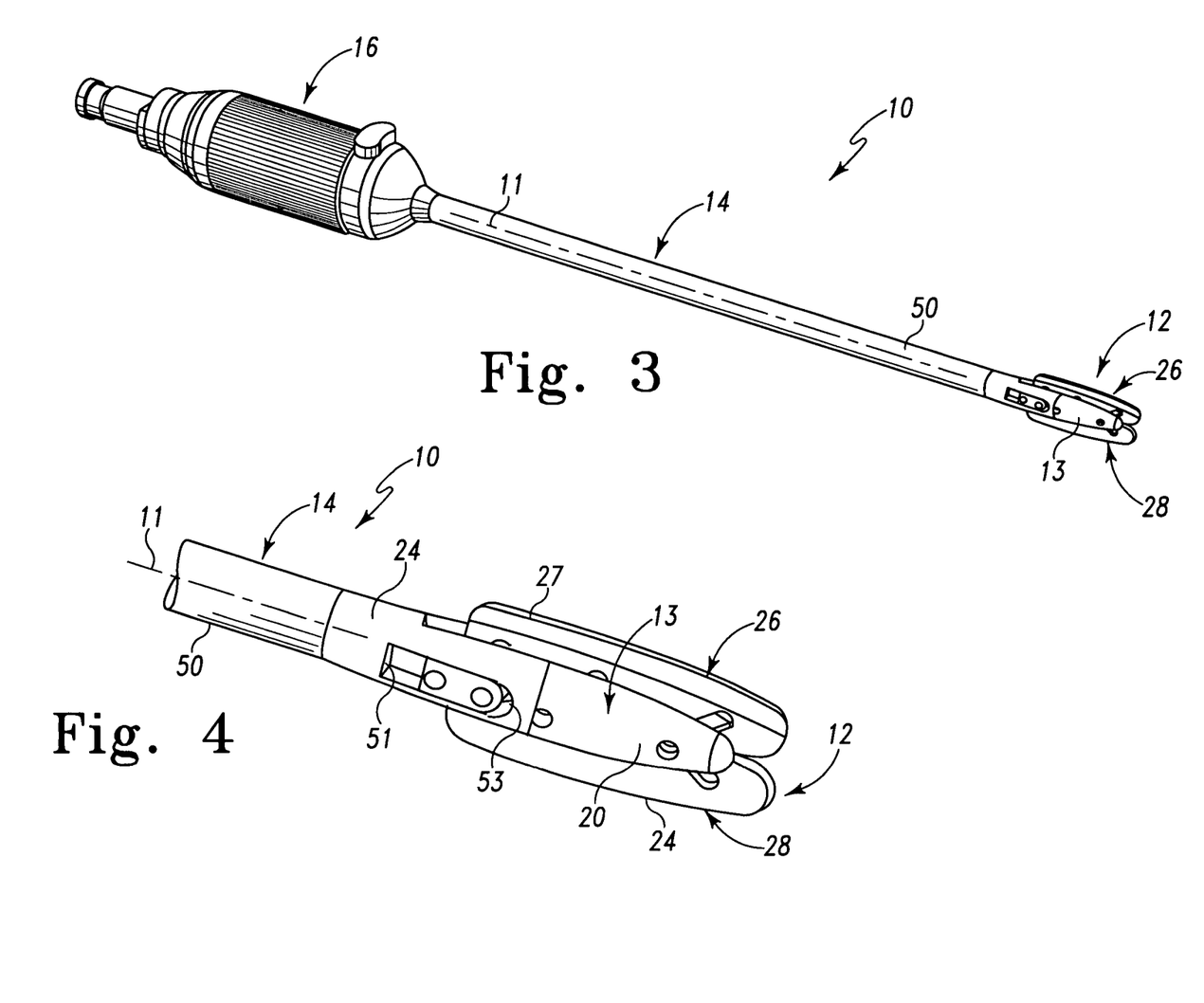
FIG. 3 is a perspective view of the cutting instrument of FIG. 1 in a deployed position.
FIG. 4 is a perspective view of the distal portion of the cutting instrument of FIG. 1 in a deployed position.

Referring to FIG. 1, there is shown an endplate cutting instrument 10. Cutting instrument 10 includes a distal cutting system 12, a proximal handle assembly 16, and an actuating assembly 14 extending therebetween. Cutting system 12 is positionable in a desired operative location, such as a spinal disc space between adjacent endplates of a pair of opposing vertebrae, in minimally invasive approaches. Non-minimally invasive approaches are also contemplated, however. Cutting system 12 includes an undeployed position, as shown in FIGS. 1 and 2, for insertion through a passageway through skin and tissue to the desired operative location. Cutting instrument 10 can be manipulated to move cutting system 12 to a deployed position, as shown in FIGS. 3 and 4, where the cutting members project outwardly for cutting of hard and soft tissue material, including vertebral endplates and disc material. Cutting instrument 10 can be rotated about its longitudinal axis 11 to rotate the cutting members to effect a cutting action along the adjacent bony or soft tissue material. When the desired cutting has been completed, cutting instrument 10 can be manipulated to return cutting system 12 to its undeployed position for repositioning at the operative location for further cutting or for withdrawal from the patient through the passageway.

As shown in FIGS. 3 and 4, cutting system 12 includes at least one first cutting member 26 and at least one second cutting member 28. First cutting member 26 includes a cutting blade 27 extending along one side thereof. Second cutting member 28 includes a cutting blade 29 extending along one side thereof, which is positioned in a direction opposite cutting blade 27 when assembled with instrument 10. Other embodiments contemplate that two or more of the cutting members 26 and/or cutting members 28 are positioned directly adjacent one another, or spaced from one another with intervening ones of the other cutting member 26, 28. Still other embodiments contemplate a cutting instrument 10 with one or more cutting members that extend in only one direction when the one or more cutting members are deployed.

In the illustrated embodiment, cutting blades 27, 29 provide a sharp, knife-like edge along the respective cutting member 26, 28. Other shapes and forms are also contemplated for cutting blades 27, 29. For example, cutting blades 27, 29 could include a plurality or series of elongated blades or sharp edges that extend transversely to longitudinal axis 11 of cutting instrument 10. In another example, cutting blades 27, 29 include one or more sharp or serrated edges that extend along the longitudinal axis 11 of cutting instrument 10.

In the undeployed position of FIG. 2, cutting members 26, 28 are substantially enclosed within a mounting portion 13 at the distal end of cutting instrument 10. When enclosed, mounting portion 13 prevents cutting blades 27, 29 from contacting tissue or other anatomical structures as cutting system 12 is advanced to the desired location at the operative site. To obtain the deployed position of FIGS. 3 and 4, cutting blades 27, 29 are moved transversely to longitudinal axis 11 to extend outwardly from mounting portion 13 where cutting blades 27, 29 can engage the adjacent bony structure and other tissue for cutting.

Cutting blades 27, 29 can at least partially cut, scrape or remove the bony material or other tissue of the vertebral endplates and the intradiscal space when deployed and moved upon rotation of cutting instrument 10 about its longitudinal axis 11. Cutting instrument 10 can shape the endplates and the intradiscal space to receive an implant device, graft material, or other implant or material. Cutting blades 27, 29 can be withdrawn and redeployed at various heights relative to longitudinal axis 11 as may be needed to provide the desired removal of bone material of the endplates. It is further contemplated that cutting instrument 10 can be manipulated by, for example, rotating it about longitudinal axis 11, with cutting blades 27, 29 deployed to provide endplate cutting. For example, cutting instrument 10 can be rotated a number of times 360 degrees about longitudinal axis 11 with cutting blades 27, 29 deployed, or rotated back and forth in small strokes of less than 180 degrees with cutting blades 27, 29 deployed. When the desired cutting has been obtained, cutting blades 27, 29 can be withdrawn into mounting portion 13, allowing withdrawal of cutting system 12 from the disc space and the patient's body without exposing tissue, nerves and other anatomical structures to cutting blades 27, 29.

Figure 5:
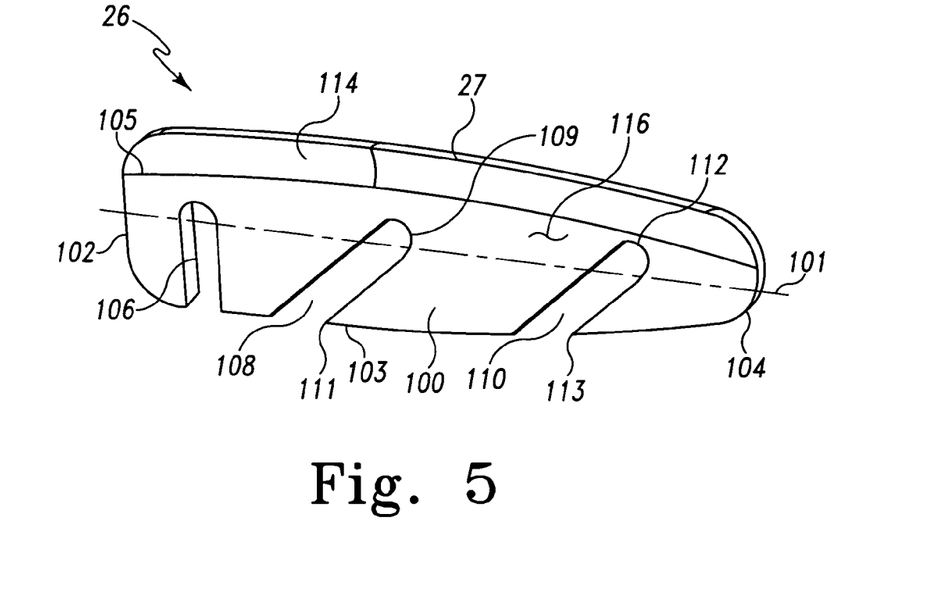
FIG. 5 is a perspective view showing a cutting member comprising a portion of the instrument of FIG. 1.

Referring to FIG. 5, further details regarding first cutting member 26 will be provided, it being understood that second cutting member 28 can be substantially identical thereto. Cutting member 26 includes an elongated body portion 100 extending between a proximal end 102 and a distal end 104 along longitudinal axis 101. Cutting blade 27 extends along and includes a slight convex curvature along longitudinal axis 101. Cutting blade 27 further extends along an outer side 105 of body portion 100. Body portion 100 includes an inner side 103 extending along longitudinal axis 101 opposite cutting blade 27. Inner side 103 includes a smooth surface profile along longitudinal axis 101. To facilitate insertion through the surgical approach when cutting member 26 is in its undeployed position in mounting portion 13, inner side 103 can includes a curved profile adjacent distal end 104 so that distal end 104 has a blunt nose and reduced height relative to proximal end 102. Outer side 105 extends along a substantially uniform, gradual curve along longitudinal axis 101. Inner side 103 is more aggressively curved adjacent distal end 104, offsetting the blunt nose at distal end 104 toward outer side 105 relative to longitudinal axis 101.

Body portion 100 includes a proximal slot 106 orthogonally oriented to longitudinal axis 101 and opening on inner side 103. Body portion 100 further includes a proximal passage 108 and a distal passage 110. Passages 108, 110 are inclined relative to longitudinal axis 101 so that passage 108 intersects longitudinal axis 101, and includes a distal end 109 and a proximal end 111. Passage 110 also intersects longitudinal axis 101, and includes a distal end 112 and a proximal end 113. Distal ends 109, 112 form a terminal end of the respective passage that is offset toward outer side 105 from longitudinal axis 101, and proximal ends 111, 113 are offset from longitudinal axis 101 and open along inner side 103.

Figure 6:
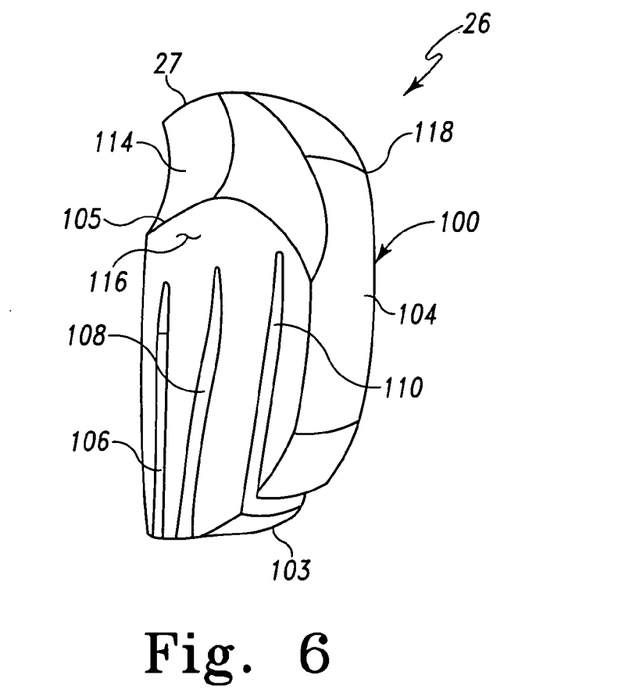
FIG. 6 is a perspective view looking endwise at the cutting member of FIG. 5.

As shown in FIG. 6, cutting member 26 includes a concave recess 114 formed in a first sidewall 116 adjacent cutting blade 27. Cutting blade 27 extends toward first sidewall 116 so that as cutting blade 27 is rotated in the direction of first sidewall 116 it removes bony material. Cutting blade 27 can include a smooth, convex curvature along second sidewall 118 such that cutting blade 27 does not cut into the adjacent tissue when rotated in the direction of second sidewall 118. Concave recess 114 provides a receptacle for holding and directing material removed from the adjacent vertebral endplates away from cutting blade 27 as cutting blade 27 is rotated thereagainst.

Figure 7:
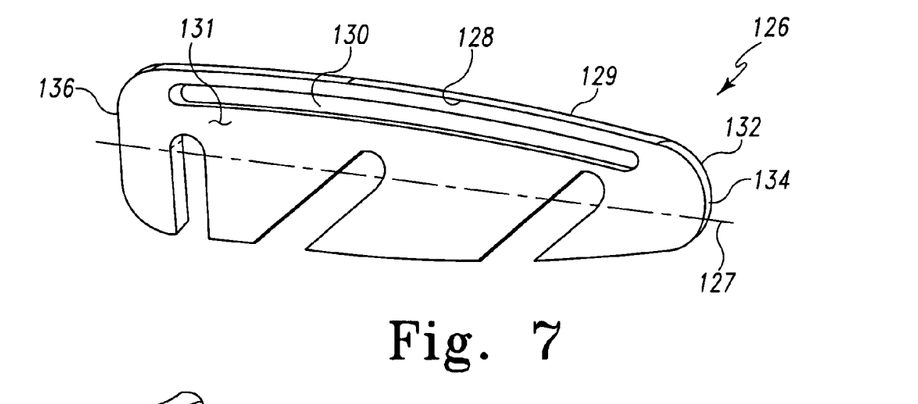
FIG. 7 is a perspective view of another embodiment cutting member.

In FIG. 7 there is shown an another embodiment cutting member 126. Cutting member 126 is substantially identical to cutting member 26, but provides a different blade configuration. Cutting member 126 extends along longitudinal axis 127, and includes a cutting blade 128 extending along on outer side 129 thereof. A longitudinal slot 130 extends between opposite sidewalls 131, 132 of cutting member 126. Slot 130 extends along and adjacent to cutting blade 128, and includes opposite terminal ends adjacent distal end 134 and proximal end 136 of cutting member 126. Slot 130 provides a passage through which tissue material removed by cutting blade 128 can pass for deposit behind cutting blade 128 as it is rotated about longitudinal axis 11 of cutting instrument 10. Slot 130 reduces the potential of clogging of cutting blade 128 and maintains its ability to cut tissue material with several repeated passes along the adjacent tissue material.

Figures 8, 8A, 8B:
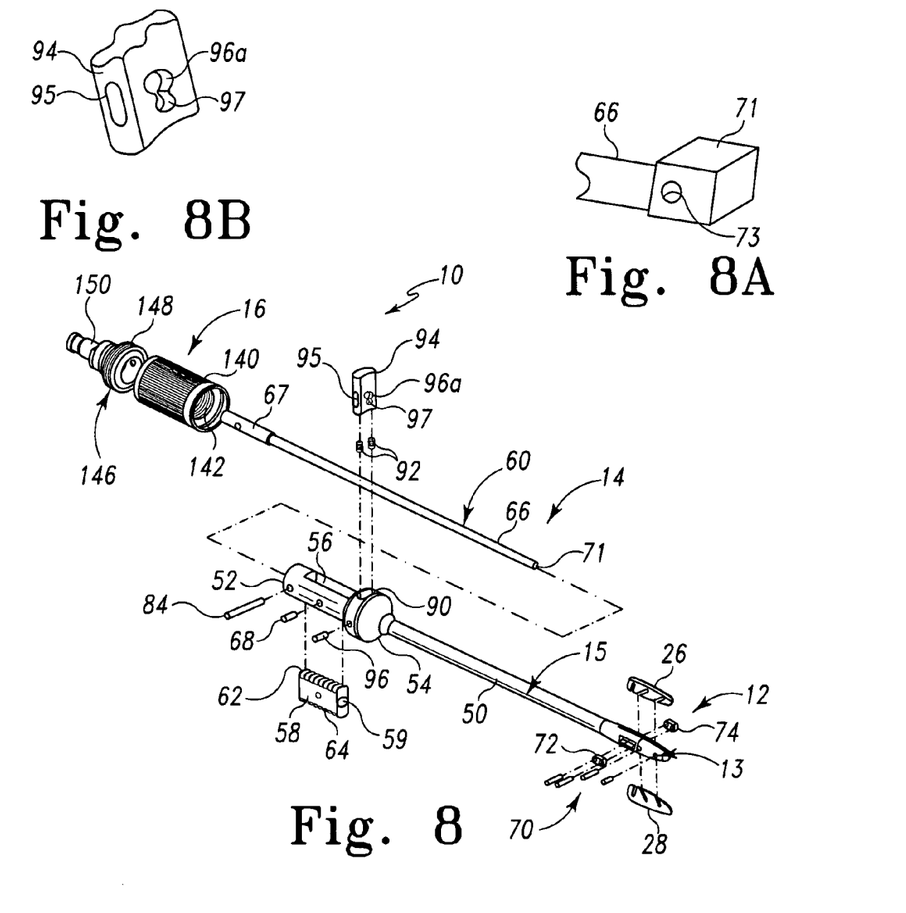
FIG. 8 is an exploded perspective view of the cutting instrument of FIG. 1.
FIG. 8A is a perspective view of a drive member at a distal end of an actuating member of the cutting instrument of FIG. 8.
FIG. 8B is a perspective view of a portion of a release member of the cutting instrument of FIG. 8.
Figure 9:
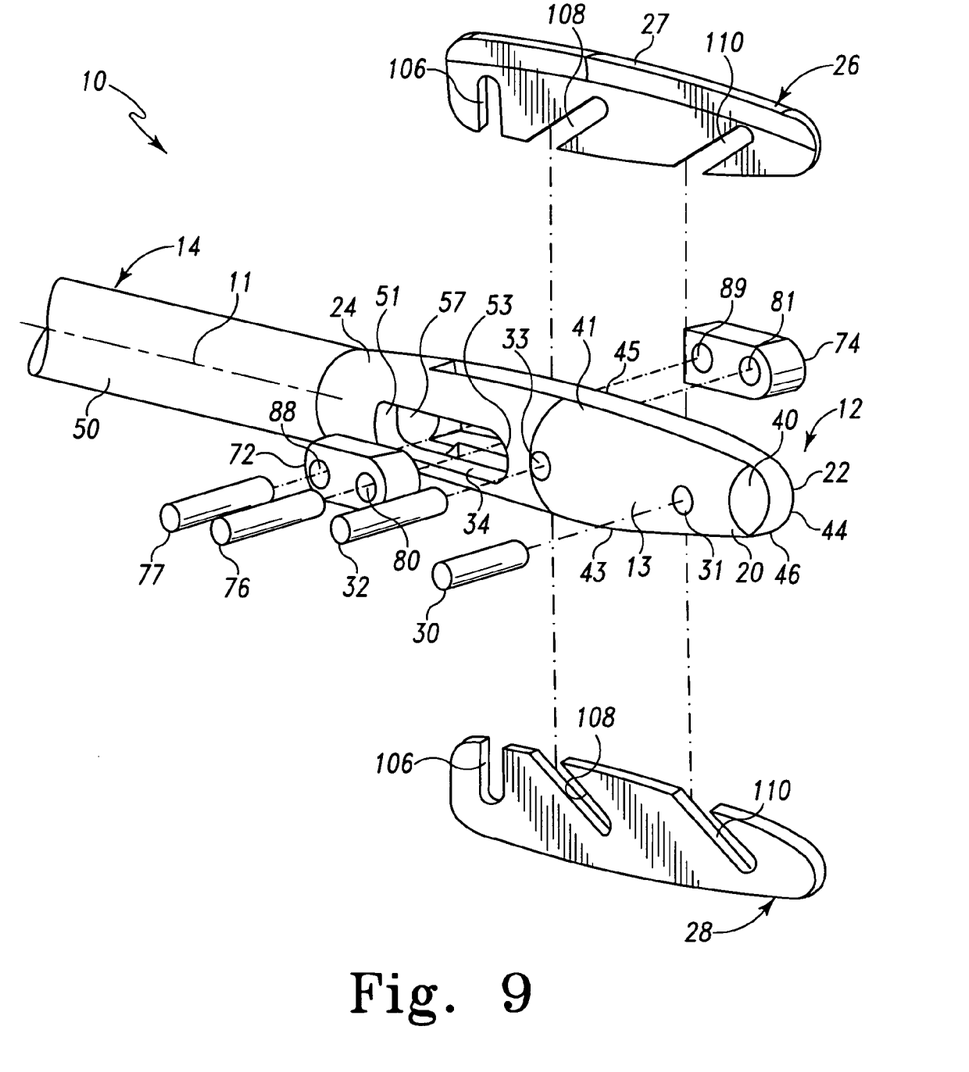
FIG. 9 is an exploded perspective view of the distal portion of the cutting instrument of FIG. 1.

Referring further to FIGS. 8-9, mounting of cutting system 12 to mounting portion 13 of instrument 10 will be further described. Mounting portion 13 is provided at the distal end of a mounting member 15 of actuator assembly 14. Mounting member 15 includes a shaft 50 extending between a proximal coupling member 52 and mounting portion 13. Mounting portion 13 includes a first flange member 20 spaced from a second flange member 22. Flange members 20, 22 extend distally from an end member 24 at the distal end of shaft 50. Flange members 20, 22 extend along and are offset laterally from longitudinal axis 11, providing upper and lower openings and a distal end opening therebetween. Flange member 20 includes distal end nose 40 having a blunt rounded shape, and flange member 22 includes distal end nose 44 having a blunt rounded shape. The blunt rounded shape of end noses 40, 44 facilitates insertion through tissue and into the space between adjacent vertebrae.

Flange member 20 includes a side opening 34 extending from a distal end wall 51 of end member 24 distally along a portion of the length of flange member 20 to an intermediate end wall 53. Similarly, flange member 22 includes a side opening (not shown) extending from distal end wall 51 of end member 24 along a portion of the length of flange member 22 to an intermediate end wall in flange member 22. The side openings are identical to one another and aligned with one another along longitudinal axis 11.

A coupling assembly 70 is provided to couple cutting members 26, 28 to an actuator 60 movably received through shaft 50 of mounting member 15. Actuating member 60 includes a shaft 66 and coupling assembly 70 at a distal end of shaft 66. Shaft 66 is positionable in a bore 57 (FIG. 9) extending through shaft 50 of mounting member 15 that opens at distal end wall 51 of end member 24. As shown in further detail in FIG. 8A, coupling assembly 70 includes a drive member 71 at a distal end of shaft 66. A first linkage plate 72 extends distally from one side of drive member 71, and a second linkage plate 74 extends distally from the opposite side of drive member 71. Linkage plate 72 includes a proximal hole 88, and linkage plate 74 includes a proximal hole 89. Drive member 71 includes a drive member hole 73 extending therethrough alignable with proximal holes 88, 89 of linkage plates 72, 74. A drive member pin 77 extends through the aligned holes 88, 73, 89 to couple linkage plates 72, 74 to drive member 71. When assembled, linkage plates 72, 74 are received in corresponding ones of the side openings of flange members 20, 22, and movable proximally and distally therein in response to proximal and distal movement of drive member 71.

First linkage plate 72 further includes a distal hole 80, and second linkage plate 74 includes a distal hole 81. Linkage pin 76 extends through aligned proximal slots 106 of cutting members 26, 28 and distal holes 80, 81 of linkage plates 72, 74. Cutting members 26, 28 are coupled to actuator 60 through drive member 71 and movable therewith between flange members 20, 22 in response to proximal and distal movement of drive member 71 along longitudinal axis 11.

Guide pins are further provided to mount cutting members 26, 28 between flange members 20, 22 for movement between the deployed and undeployed positions. A distal guide pin 30 extends between and is secured in aligned holes 31 adjacent the distal end noses 40, 44 of flange members 20, 22. A proximal guide pin 32 extends between and is secured in aligned holes 33 located about mid-length along flange members 20, 22 and distally of side openings 34. Cutting members 26, 28 are movably mounted to flange members 20, 22 with distal guide pin 30 extending through aligned distal passages 110 of cutting members 26, 28. Proximal guide pin 32 extends through aligned proximal passages 108 of cutting members 26, 28.

Drive member 71 of coupling assembly 70 is positioned distally of distal end wall 51 of end member 24 between flange members 20, 22 when assembled. Linkage pin 76 of coupling assembly 70 extends through aligned proximal slots 106 of cutting members 26, 28. When cutting members 26, 28 are in their undeployed position, drive member 71 is adjacent end wall 51 and linkage pin 76 is positioned adjacent the outer terminal ends of proximal slots 106. Distal guide pin 30 is located adjacent distal ends 112 of aligned distal passages 110 of cutting members 26, 28. Proximal guide pin 32 is located adjacent the distal ends 109 of aligned proximal passages 108 of cutting members 26, 28. In this undeployed position, cutting members 26, 28 are retracted relative to flange members 20, 22 so that cutting blade 27 is recessed at or below the upper ends 41, 45 of flange members 20, 22, and cutting blade 29 is recessed at or below the lower ends 43, 46 of flange members 20, 22, as shown in FIG. 2. In the undeployed position, the reduced height distal ends 104 of cutting members 26, 28 are substantially aligned with the rounded distal end noses 40, 44 of flange members 20, 22, as shown in FIG. 2. This provides cutting system 12 with a tapered leading end having smooth surface profile, facilitating insertion of mounting portion 13 into a spinal disc space. It is contemplated that flange members 20, 22 can facilitate recapitulation of a collapsed disc space as it is inserted therein.

When deployed, actuating member 60 is moved distally relative to mounting member 15, thereby advancing drive member 71 and flange plates 72, 74 distally between flange members 20, 22 in side openings 34. Linkage pin 76 pushes distally on cutting members 26, 28 in proximal slots 106. This distal movement advances cutting members 26, 28 along guide pins 30, 32 so that guide pins 30, 32 are moved toward proximal ends 113, 111 of passages 110, 108. The sloped orientation of passages 108, 110 offsets the distal ends relative to longitudinal axis 101 of cutting members 26, 28. This causes cutting members 26, 28 to move upwardly and downwardly, respectively, and away from longitudinal axis 11 in parallel relation as drive member 71 is moved distally along longitudinal axis 11 with actuator 60. Cutting members 26, 28 are thus displaced distally and away from longitudinal axis 11 to advance cutting blades 27, 29 outwardly from the upper ends 41, 45 and lower ends 43, 46 of flange members 20, 22.

As shown in FIGS. 3 and 4, cutting member 26 moves upwardly through the upper opening between flange members 20, 22 when moving to the deployed position, and cutting member 28 moves downwardly through the lower opening between flange members 20, 22 when moving to the deployed position. Cutting members 26, 28 also move distally relative to flange members 20, 22 so that distal ends 104 extend distally past distal ends 40, 44 of flange members 20, 22 through the distal opening between flange members 20, 22. It is contemplated that cutting members 26, 28 move parallel to longitudinal axis 11 of cutting instrument 10 during deployment so that the entire length of cutting members 26, 28 can contact the adjacent vertebral endplate to provide cutting thereto when deployed. In addition, deployment of cutting members 26, 28 can be stopped at any location between their undeployed position and fully deployed position, and can be maintained at this intermediate position for cutting of tissue material.

The mounting arrangement between mounting portion 13 and cutting members 26, 28 facilitates the application of sufficient force to cutting members 26, 28 so that cutting blades 27, 29 can cut bony structure and other tissue when deployed and rotated. Guide pins 30, 32 provide multiple support locations in the passages 110, 108 of cutting members 26, 28 to maintain parallel movement of the cutting members 26, 28 relative to longitudinal axis 11 throughout the range of motion between deployed and undeployed positions. Linkage pin 76 maintains contact in proximal slots 106 of cutting members 26, 28, and actuator 60 is configured as discussed below to prevent cutting members 26, 28 from moving toward their undeployed position when external forces are applied thereto during use.

Referring back to FIG. 8, the proximal portion of actuating assembly 14 and proximal handle assembly 16 will be discussed. Actuating assembly 14 includes mounting member 15 and actuating member 60 movably received in bore 57 extending through shaft 50 of mounting member 15. Actuating member 60 includes a shaft member 66 having an enlarged proximal portion 67. Mounting member 15 includes a coupling member 52 at a proximal end of shaft 50, and a hub 54 between coupling member 52 and shaft 50. Coupling member 52 includes a receptacle 56 extending therethrough and opening along opposite sides thereof. A translation member 58 is received in receptacle 56 and non-rotatably captured therein. Translation member 58 includes an axial bore 59 extending along longitudinal axis 11 when assembled in receptacle 56. Enlarged proximal portion of shaft 66 is positionable into axial bore 59 with shaft member 66 extending through bore 57 of shaft 50.

A translation member pin 68 extends through translation member 58, and couples enlarged proximal portion 67 of shaft 66 to translation member 58. Translation member 58 is non-rotatably received in receptacle 56, but has a length relative to receptacle 56 such that translation member 58 and thus actuating member 60 coupled thereto can axially translate between opposite proximal and distal ends of receptacle 56. Translation member 58 includes upper and lower threaded surfaces 62, 64.

Proximal handle assembly 16 further includes an outer sleeve 140 positionable about coupling member 52. Outer sleeve 140 includes an inner threaded bore 142 that threadingly engages upper and lower surfaces 62, 64 of translation member 58. A handle coupler 146 is attached to the proximal end of sleeve 140. Handle coupler 146 includes a proximal collar 148 mounted to a proximal end of sleeve 140 and a handle connector 150 extending proximally from collar 148. Sleeve 140 is rotatably captured between proximal collar 148 and hub 54. Handle connector 150 can be configured as a Hudson-type connector for releasable attachment of a T-handle or other device to facilitate insertion, rotation, manipulation or withdrawal of cutting instrument 10. A handle pin 84 extends through proximal collar 148 and coupling member 52 to secure coupling member 52 and thus mounting member 15 axially to handle coupler 146 and sleeve 140.

When assembled, the surgeon can rotate sleeve 140 about translation member 58 to axially translate translation member 58 proximally and distally in receptacle 56. The inner threaded bore of sleeve 140 engages the threaded surfaces 62, 64 of translation member 58 to translate the axial rotation of sleeve 140 into axial translation of translation member 58. The proximal and distal translation of translation member 58 in turn proximally and distally translates actuator member 60 along longitudinal axis 11, which in turn moves drive member 71 proximally and distally along longitudinal axis 11, which causes retraction and deployment of cutting members 26 relative to mounting portion 13, as discussed above.

Hub 54 includes a hub receptacle 90 opening on one side thereof. Hub receptacle 90 receives a pair of spring members 92 therein. A release member 94 is positionable in hub receptacle 90 in contact with spring members 92. Spring members 92 bias release member 94 so that the end of release member 94 opposite spring members 92 normally protrudes out of receptacle 90. A release member pin 96 is positionable through hub 54 and into release member slot 95, as shown in FIG. 8B. Slot 95 allows release member 94 to translate into and out of hub receptacle 90. Pin 96 captures release member 94 in receptacle 90 and contacts the lower end of slot 95 to capture release member 94 in receptacle 90. When release member 94 is depressed against the bias of spring members 92, pin 96 translates along slot 95 toward its upper end.

Release member 94 includes an actuating member passage having a first portion 96a and a second portion 97. Shaft 66 of actuating member 60 is normally received in second portion 97, and is movable axially relative to second portion 97. The enlarged proximal shaft portion 67 of shaft 66 cannot be positioned into second portion 97. Accordingly, distal axial translation of actuating member 60 is limited by contact of the distal end of proximal shaft portion 67 with release member 94 about second portion 97 of the actuating member passage of release member 94. This limits translation of actuating member 60 distally along longitudinal axis 11 to maintain guide pins 30, 32 distally of the proximal ends of passages 110, 108 of cutting members 26, 28, and also maintains linkage pin 76 within proximal slots 106 of cutting members 26, 28. As shown in FIG. 3, linkage plates 72, 74 are spaced proximally of the distal ends of openings 34 when cutting members 26, 28 are fully deployed.

Figure 10:
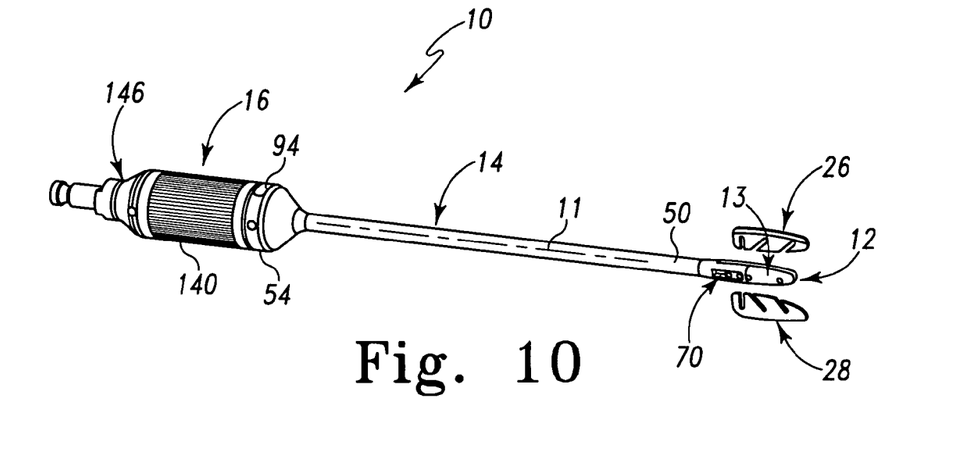
FIG. 10 is a perspective view of the cutting instrument of FIG. 1 manipulated for removal of the cutting members.
Figure 11:
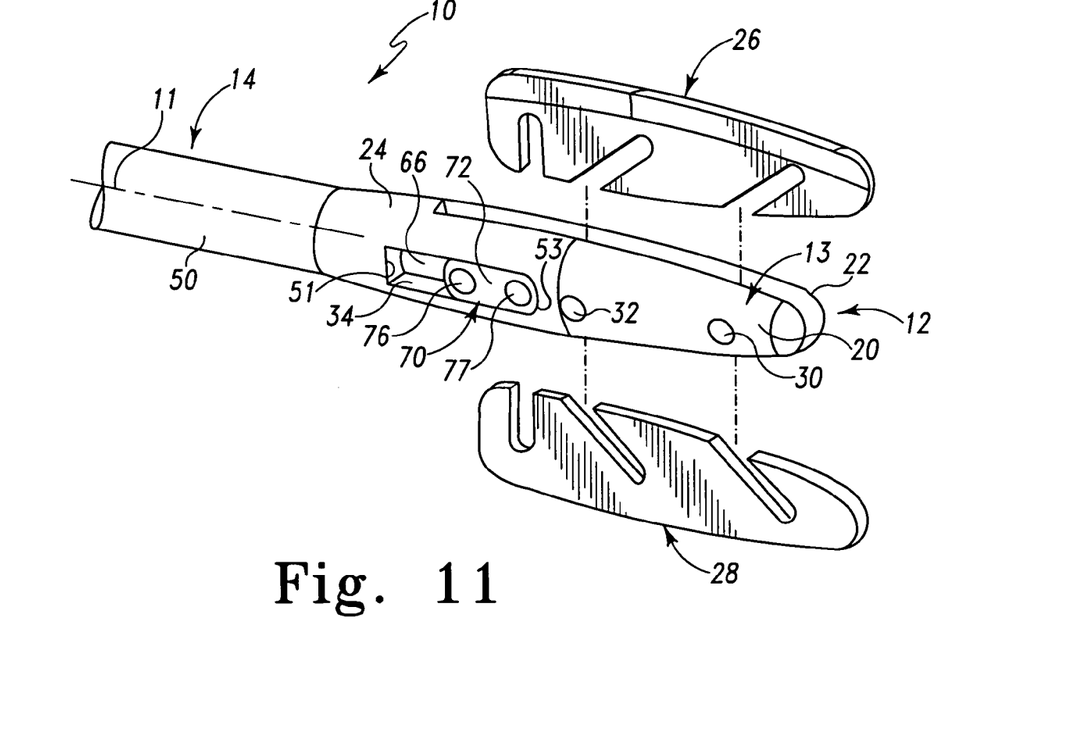
FIG. 11 is a view of the distal portion of the cutting instrument of FIG. 10 with the blades removed.

The distal translation of actuating member 60 and thus the deployment of cutting members 26, 28 are thus also limited by the contact of enlarged shaft portion 67 with second portion 97 of the release member passage. Since slots 106 and passages 108, 110 of cutting members 26, 28 are open along inner side 103, cutting members 26, 28 can be removed from mounting portion 13 by translating drive member 71 and cutting members 26, 28 distally far enough to align the open sides of slots 106 and passages 108, 110 with the respective pin 76, 32, 30 extending therethrough. Accordingly, release member 94 can be depressed against the bias of spring members 82 to align first portion 96a of the release member passage with enlarged shaft portion 67. first portion 96a is larger than second portion 97 and allows passage of enlarged shaft portion 67 therethrough. Accordingly, when release member 94 is depressed as shown in FIG. 10, actuator 60 can be further distally translated along longitudinal axis 11 to allow blade members 26, 28 to be removed, as shown in FIGS. 10 and 11. In this release position, linkage plates 72, 74 are positioned adjacent or against the distal ends 53 of side openings 34 in flange members 20, 22. Removal of cutting members 26, 28 facilitates cleaning of instrument 10, and simple replacement of cutting members 26, 28 without discarding the entire instrument.

Figure 12:
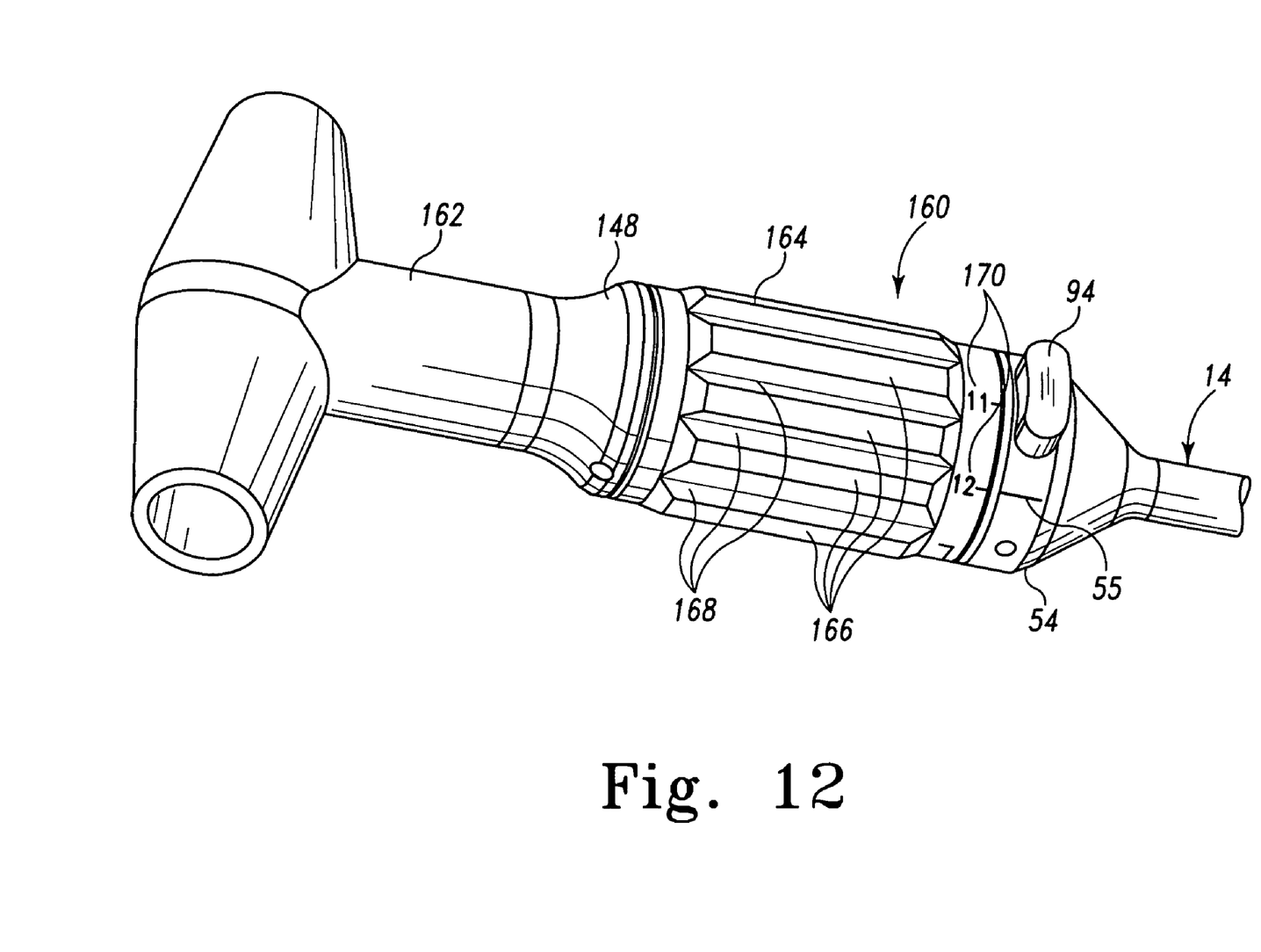
FIG. 12 is a perspective view of another embodiment of a proximal portion for the cutting instrument of FIG. 1.

Referring to FIG. 12, there is shown another embodiment handle assembly 160 which can be employed with cutting instrument 10. Handle assembly 160 includes a T-handle 162 integrally formed with or separately attachable to distal collar 148. T-handle 162 is rigidly coupled with mounting member 15, and can be manipulated to rotate cutting instrument 10 and cutting members 26, 28 about longitudinal axis 11. Handle assembly 160 further includes an outer sleeve 164 having outer surface features to facilitate gripping and rotation of sleeve 164 about axis 11 to selectively deploy and un-deploy cutting members 26, 28 from mounting portion 13. The surface features include a plurality of elongated ribs 166 separated by valleys 168. Other grip enhancing features are also contemplated, such as the knurled sleeve 140 discussed above, and sleeves which include surface coatings or textures to facilitate gripping of the sleeve. The sleeve can also be made with semi-rigid or flexible material along the outer surface there, for example, to facilitate gripping. A smooth sleeve can also be provided.

The embodiment in FIG. 12 is further provided with indicia to indicate the height between the cutting blades 27, 29 of cutting members 26, 28 at various stages of deployment of cutting members 26, 28 from mounting portion 13. For example, a calibration mark 55 can be provided on hub 54, and a series of height markings 170 can be provided about the distal end of outer sleeve 164. The height marking 170 provide an indication of the deployed height between cutting blades 27, 29 of cutting members 26, 28. This can facilitate the use of instrument 10 during surgery. For example, it may be desired to create a space between vertebrae of a certain height, or it may be desired to remove bony material with cutting members 26, 28 by incrementally increasing the height between cutting blades 27, 29 after successive passes of cutting blades 27, 29 along the bony tissue.

In one specific embodiment, it is contemplated that the maximum height of mounting portion 13 when cutting members 26, 28 are undeployed is 7 millimeters, and the height between cutting blades 27, 29 of cutting members 26, 28 when fully deployed is 12 millimeters. The cutting members can be positioned between these undeployed and fully deployed positions to provide other heights ranging from 7 millimeters to 12 millimeters. Other embodiments contemplate undeployed heights of less than 7 millimeters or more than 7 millimeters, and fully deployed heights of less than 12 millimeters or more than 12 millimeters.

It is contemplated that the cutting instruments discussed herein can be used in minimally invasive surgical techniques where the disc space is accessed through a micro-incision, a sleeve, or one or more retractors that provide a protected passageway to the disc space. The cutting instruments also have application in open surgical techniques where skin and tissue are incised and retracted to expose the surgical site. The cutting instruments can be useful in posterior approaches to a spinal disc space where tissue, nerves, and the posterior vertebral elements hinder access to the disc space. Applications in other approaches, including anterior, anterior-oblique, lateral, and postero-lateral approaches are also contemplate. The cutting instruments also have application in procedures that access any region of the spine, including the cervical, thoracic, lumbar and sacral regions.

Cutting instrument 10 can be used in minimally invasive surgical procedures where anatomical considerations make it desirable to minimize contact with the surrounding tissue. For example, a postero-lateral approach to a spinal disc space requires movement of mounting portion 13 along the delicate nerves and other tissue, and through small openings in the approach to and through the annulus of the spinal disc space. Mounting portion 13 is configured so that when blade members 26, 28 are not deployed, mounting portion 13 has a bullet shaped profile without exposed, abrupt or sharp edges. When mounting portion 13 is positioned in the spinal disc space, cutting members 26, 28 are deployed in the disc space and cutting instrument 10 manipulated to remove bony material. When cutting is completed, cutting members 26, 28 are retracted to their undeployed position in mounting portion 13 to allow removal of the instrument from the disc space while protecting the adjacent nerves and other anatomical structures from cutting members 26, 28. The low profile and smooth outer surface profile when retracted can allow bone removal in the disc space without a nerve root retractor being employed in the postero-lateral approach.

While the invention has been illustrated and described in detail in the drawings and foregoing description, the same is to be considered as illustrative and not restrictive in character. All changes and modifications that come within the spirit of the invention are desired to be protected.

What is claimed is:

1. A cutting instrument, comprising:
a handle assembly;
an actuating assembly extending distally from said handle assembly along a longitudinal axis;
a cutting system operably coupled to said actuating assembly, said cutting system including a pair of cutting members mounted in a mounting portion and movable with said actuating assembly from an undeployed position to a deployed position by displacing said cutting members distally along said longitudinal axis, said pair of cutting members each including at least one cutting blade for removing tissue material upon rotation about said longitudinal axis when in said deployed position, wherein in said undeployed position said cutting blades are recessed in said mounting portion and in said deployed position said cutting members are moved away from one another by said actuating system transversely to said longitudinal axis while maintaining a parallel relation between said at least one cutting blade of said cutting members, wherein each of said cutting members includes:
a body portion extending along a longitudinal axis between a proximal end and a distal end, wherein said distal end of said body portion includes a tapered nose;
said cutting blade extends along one side of said body portion between said proximal end and said distal end and includes a sharp edge extending along said longitudinal axis that faces away from the cutting blade of the other of said cutting members; and
said body portion includes a distal passage positioned closer to said distal end than said proximal end and oriented transversely to said longitudinal axis of said body portion and a proximal passage oriented transversely to said longitudinal axis of said body portion and further comprising pins extending through each of said proximal and distal passages to mount said body portion to said mounting portion.

2. The instrument of claim 1, wherein each of said cutting blades is elongated and extends along substantially an entire length of said cutting member.

3. The instrument of claim 1, wherein:
said distal passage includes a distal end offset from said longitudinal axis of said body portion toward said cutting blade and a proximal end offset from said longitudinal axis of said body portion toward a side of said body opposite said cutting blade; and
said proximal passage includes a distal end offset from said longitudinal axis toward said cutting blade and a proximal end offset from said longitudinal axis toward a side of said body opposite said cutting blade.

4. The instrument of claim 3, wherein said body portion includes a slot orthogonally oriented to said longitudinal axis of said body portion and located proximally of said proximal passage of said body portion.

5. The instrument of claim 4, wherein said actuating assembly includes:
a mounting member including said mounting portion at a distal end thereof; and
an actuating member movable relative to said mounting member and coupled to said pair of cutting members, said actuating member being axially movable from a first position wherein said cutting members are in said undeployed position to a second position wherein said cutting members are in said deployed position.

6. The instrument of claim 5, wherein:
said actuating member includes a shaft and a coupling assembly at a distal end of said shaft in said mounting portion, said coupling assembly including a linkage pin;
said mounting member includes a shaft defining a bore movably receiving said actuating member therein, said mounting portion including:
a first flange member and a second flange member spaced from said first flange member, said cutting members being positioned between said first and second flange members;
a distal guide pin extending between said first and second flange members; and
a proximal guide pin extending between said first and second flange members, wherein said distal guide pin extends through said distal passages of said body portions, said proximal guide pin extends through said proximal passages of said body portions, and said linkage pin extends through said proximal slots of said body portions for axial movement with said actuating assembly to move said cutting members along said proximal and distal guide pins between said deployed and undeployed positions.

7. The instrument of claim 6, wherein said coupling assembly includes a drive member and a pair of linkage plates extending distally from opposite sides of said drive member, said linkage plates being movably received in side openings of said flange members, said linkage pin extending between said linkage plates distally of said drive member.

8. The instrument of claim 1, wherein each of said distal ends of said cutting blades extends distally beyond a distal end of the mounting portion when the cutting members are in the deployed position.

9. The instrument of claim 1, wherein each of said cutting members includes:

a body portion extending along a longitudinal axis between a proximal end and a distal end; and a slot adjacent said cutting blade, said slot extending along said longitudinal axis of said body portion and between opposite sidewalls of said body portion between said proximal and distal ends thereof.

10. The instrument of claim 1, wherein in said undeployed position said noses are substantially aligned with one another along a longitudinal axis of the cutting instrument and in said deployed position each of said noses are advanced distally and offset from one another on opposite sides of said longitudinal axis.

11. The instrument of claim 1, wherein said cutting members are moved simultaneously between the undeployed position and to deployed position.

12. The instrument of claim 1, wherein said cutting members are moved in a direction opposite one another when moved from the undeployed position to the deployed position.

13. A cutting instrument, comprising:
a handle assembly;
an actuating assembly extending distally from said handle assembly along a longitudinal axis;
a cutting system operably coupled to said actuating assembly, said cutting system including a pair of cutting members mounted in a mounting portion and movable with said actuating assembly from an undeployed position to a deployed position by displacing said cutting members distally along said longitudinal axis, said pair of cutting members each including at least one cutting blade for removing tissue material upon rotation about said longitudinal axis when in said deployed position, wherein in said undeployed position said cutting blades are recessed in said mounting portion and in said deployed position said cutting members are moved away from one another by said actuating system transversely to said longitudinal axis while maintaining a parallel relation between said at least one cutting blade of said cutting members, wherein each of said cutting members includes:

a body portion extending along a longitudinal axis between a proximal end and a distal end; and said body portion including a distal passage positioned closer to said distal end than said proximal end and oriented transversely to said longitudinal axis of said body portion and a proximal passage oriented transversely to said longitudinal axis of said body portion and further comprising pins extending through each of said proximal and distal passages to mount said body portion to said mounting portion.

14. The instrument of claim 13, wherein for each of said cutting members:
said distal passage includes a distal end offset from said longitudinal axis of said body portion toward said cutting blade and a proximal end opening along a side of said body portion opposite said cutting blade; and
said proximal passage includes a distal end offset from said longitudinal, axis of said body portion toward said cutting blade and a proximal end opening along a side of said body portion opposite said cutting blade.

15. The instrument of claim 14, wherein for each of said cutting members:
said body portion includes a slot orthogonally oriented to said longitudinal axis of said body portion and located proximally of said proximal passage, said slot opening along a side of said body portion opposite said cutting blade.

16. The instrument of claim 15, wherein said actuating assembly includes:
a mounting member including a distal mounting portion with a pair of flange members defining an opening therebetween, said cutting members being mounted to said flange members with proximal and distal guide pins extending between said flange members through said proximal and distal passages of said, cutting members; and
an actuating member coupled to said slot of said cutting members, said actuating member being movable relative to said mounting member from a first position wherein said cutting members are in said undeployed position to a second position wherein said cutting members are in said deployed position.

17. The instrument of claim 16, wherein:
said actuating member includes a shaft and a coupling assembly at a distal end of said shaft in said mounting portion, said coupling assembly including a pair of linkage plates movably received in side openings of said flange members and a linkage pin extending between linkage plates through said proximal slots of said cutting members.

18. A cutting instrument, comprising:
a handle assembly;
an actuating assembly extending distally from said handle assembly along a longitudinal axis, wherein said actuating assembly further includes a translation member in a receptacle defined by said coupling member, said actuating member being coupled to said translation member, said translation member being movable proximally and distally in said receptacle of said coupling member to move said actuating member proximally and distally in said bore of said mounting member and said handle assembly includes a sleeve having an inner threaded bore engaged with at least one threaded surface of said translation member, said sleeve being rotatable about said translation member to move said translation member axially between proximal and distal ends of said receptacle, wherein said mounting member includes a hub extending thereabout adjacent distal end of said sleeve, said hub defining a release member receptacle in communication with said bore; and
a cutting system operably coupled to said actuating assembly, said cutting system including a pair of cutting members mounted in a mounting portion and movable with said actuating assembly from an undeployed position to a deployed position, said pair of cutting members each including at least one cutting blade for removing tissue material upon rotation about said longitudinal axis when in said deployed position, wherein in said undeployed position said cutting blades are recessed in said mounting portion and in said deployed position said cutting members are moved away from one another by said actuating system transversely to said longitudinal axis while maintaining a parallel relation between said at least one cutting blade of said cutting members, wherein said actuating assembly includes an elongate actuating member axially and movably received in a bore of an elongate mounting member, said mounting member including said mounting portion at a distal end thereof and a proximal coupling member, said bore extending through said coupling member.

19. The instrument of claim 18, further comprising a release member movably captured in said receptacle, said release member including a passage through which said actuating member extends.

20. The instrument of claim 19, wherein said actuating member includes an enlarged proximal portion proximal of said release member passage, said enlarged proximal portion being sized to prevent passage of said enlarged proximal portion through said passage of said release member to limit distal movement of said actuating member along said longitudinal axis.

21. The instrument of claim 20, wherein said passage of said release member includes a second portion in communication with a first portion of said passage, said actuating member being received in said first portion and said release member being movable to align said second portion with said enlarged proximal portion of said actuating member, said second portion being sized to receive said enlarged proximal portion of said actuating member therethrough to allow said actuating member to be displaced distally along said longitudinal axis through said second portion to a release position, wherein in said release position said cutting members are removable from said mounting portion.

22. A cutting instrument, comprising:
a handle assembly including a rotatable sleeve and a proximal handle;
an actuating assembly extending distally from said handle assembly along a longitudinal axis, said actuating assembly including:
a proximal coupling member defining a receptacle;
a translation member non-rotatably received and axially moveable in said receptacle, said sleeve being positioned distally of said proximal handle and threadingly engaged and rotatable about said translation member to axially translate said translation member in said receptacle;
an actuating member coupled to said translation member and axially movable therewith, wherein said actuating assembly includes a mounting member and said actuating member extends through a bore of said mounting member, said mounting member including said mounting portion at a distal end thereof and said coupling member at a proximal end thereof, said mounting member further including a hub extending thereabout distally of said coupling member, said hub defining a release member receptacle in communication with said bore; and
a cutting system operably coupled with a distal end of said actuating member, said cutting system including a pair of cutting members mounted in a mounting portion and movable with said actuating assembly from an undeployed position to a deployed position, said pair of cutting members each including at least one cutting blade for removing tissue material upon rotation about said longitudinal axis when in said deployed position.

23. The instrument of claim 22, wherein in said undeployed position said cutting blades are recessed in said mounting portion and in said deployed position said cutting members are moved simultaneously along and transversely to said longitudinal axis by said actuating system to position said cutting blades outside said mounting portion with said cutting blades providing a sharp edge extending along said longitudinal axis and said sharp edges face away from one another.

24. The instrument of claim 22, wherein said cutting blades are moved in parallel relation to one another between said undeployed and deployed positions, wherein said cutting blades include sharp edges that extend along said longitudinal axis and said sharp edges face in opposite directions from one another.

25. The instrument of claim 22, wherein said sleeve includes an inner threaded bore engaged with at least one threaded surface of said translation member.

26. The instrument of claim 22, further comprising a release member movably captured in said receptacle, said release member includes a passage through which said actuating member extends.

27. The instrument of claim 26, wherein said actuating member includes an enlarged proximal portion proximal of said release member passage, said enlarged proximal portion being sized to prevent passage of said enlarged proximal portion through said passage of said release member to limit distal movement of said actuating member along said longitudinal axis.

28. The instrument of claim 27, wherein said passage of said release member includes a second portion in communication with a first portion of said passage, said actuating member being normally received in said first portion and said release member being movable to align said second portion with said enlarged proximal portion of said actuating member, said second portion being sized to receive said enlarged proximal portion of said actuating member therethrough to allow said actuating member to be displaced distally along said longitudinal axis through said second portion to a release position, wherein in said release position said cutting members are removable from said mounting portion.

29. A cutting instrument, comprising:
a handle assembly including a rotatable sleeve and a proximal handle;
an actuating assembly extending distally from said handle assembly along a longitudinal axis, said actuating assembly including:
a mounting member with a mounting portion at a distal end thereof and a hub at a proximal end thereof, said mounting member including a bore extending therethrough, wherein said hub defines a release member receptacle in communication with said bore of said mounting member;
an actuating member extending through said bore and being coupled to said sleeve distally of said proximal handle, said actuating member being axially movable in said bore relative to said mounting member in response to rotation of said sleeve about said longitudinal axis; and
a cutting system operably coupled at a distal end of said actuating member, said cutting system including a pair of cutting members mounted in said mounting portion and movable with said actuating assembly from an undeployed position to any one of a plurality of deployed positions, each of said deployed positions defining a height between cutting blades of said cutting members, said cutting blades operable to remove tissue material upon rotation about said longitudinal axis when in said deployed position, wherein one of said sleeve and said hub includes indicia indicating said height based upon a rotational position of said sleeve relative to said hub.

30. The instrument of claim 29, wherein in said undeployed position said cutting blades are recessed in said mounting portion and in said deployed position said cutting members are moved simultaneously along and transversely to said longitudinal axis by said actuating system to position said cutting blades outside said mounting portion.

31. The instrument of claim 29, wherein said cutting blades are moved in parallel relation to one another between said undeployed and deployed positions.

32. The instrument of claim 29, wherein said mounting member includes a coupling member extending proximally from said hub, said coupling member defining a receptacle and further comprising a translation member in said receptacle coupled to said actuating member.

33. The instrument of claim 32, wherein said sleeve includes an inner threaded bore engaged with at least one threaded surface of said translation member, said translation member being axially movable in said receptacle upon rotation of said sleeve thereby axially moving said actuating member relative to said mounting member.

34. The instrument of claim 29, further comprising a release member movably captured in said receptacle, said release member includes a passage through which said actuating member extends.

35. The instrument of claim 34, wherein said actuating member includes an enlarged proximal portion proximal of said release member passage, said enlarged proximal portion being sized to prevent passage of said enlarged proximal portion through said passage of said release member to limit distal movement of said actuating member along said longitudinal axis.

36. The instrument of claim 35, wherein said passage of said release member includes a second portion in communication with a first portion of said passage, said actuating member being normally received in said first portion and said release member being movable to align said second portion with said enlarged proximal portion of said actuating member, said second portion being sized to receive said enlarged proximal portion of said actuating member therethrough to allow said actuating member to be displaced distally along said longitudinal axis through said second portion to a release position, wherein in said release position said cutting members are removable from said mounting portion.

* * * * *